United States Patent [19]

Yano et al.

[11] Patent Number: 5,091,183

[45] Date of Patent: Feb. 25, 1992

[54] INSECTICIDAL AND/OR ACARICIDAL COMPOSITION

[75] Inventors: Toshihiko Yano, Ashiya; Noritada Matsuo, Itami; Yoko Torisu, Ashiya; Kazunobu Dohara, Toyonaka, all of Japan

[73] Assignee: Sumitomo Chemical Company, Limited, Osaka, Japan

[21] Appl. No.: 577,103

[22] Filed: Sep. 4, 1990

[30] Foreign Application Priority Data

Sep. 14, 1989 [JP] Japan ................................. 1-239384

[51] Int. Cl.$^5$ ............................................. A01N 25/00
[52] U.S. Cl. ........................................ 424/405; 424/45; 514/510; 514/515; 514/520; 514/531; 514/532
[58] Field of Search ............... 424/405, 45; 514/510, 514/515, 56, 531, 532

[56] References Cited

U.S. PATENT DOCUMENTS 3,899,586  8/1975  Okuno et al. ..................... 424/274
3,934,023  1/1976  Ouuno et al. ..................... 424/274
4,024,163  5/1977  Elliott et al. ..................... 260/374.4

FOREIGN PATENT DOCUMENTS 0064803  11/1982  European Pat. Off. .
50-77529  6/1975  Japan .

OTHER PUBLICATIONS

Chemical Abstracts Reference 104:104461h.

*Primary Examiner*—Thurman K. Page
*Assistant Examiner*—Louis A. Picone
*Attorney, Agent, or Firm*—Stevens, Davis, Miller & Mosher

[57] ABSTRACT

An insecticidal and/or acaricidal composition comprising as active ingredients 2-methyl-4-oxo-3-(2-propynyl)cyclopent-2-enyl chrysanthemate and a phenoxybenzyl ester compound having the formula [I],

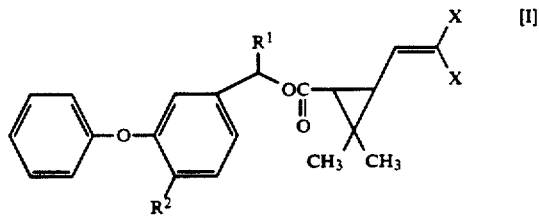

wherein $R^1$ is hydrogen or cyano, $R^2$ is hydrogen or fluorine, and X is chlorine or bromine, is markedly effective against insect pests having a low sensitivity to pyrethroid and acarine pests which cannot be effectively controlled by the use of a single agent.

1 Claim, No Drawings

INSECTICIDAL AND/OR ACARICIDAL COMPOSITION

The present invention relates to a novel insecticidal and/or acaricidal composition.

There have been known some insecticidal and/or acaricidal compositions obtained by mixing two or more pyrethroid compounds. For example, U.S. Pat. No. 3,899,586 discloses an insecticidal and/or acaricidal composition obtained by mixing N-(3,4,5,6-tetrahydrophthalimide)-methyl chrysanthemate with 5-(2-propynyl)furfuryl 3-(2,2-dichlorovinyl)-2,2-dimethylcyclopropanecarbrxylate.

In addition, U.S. Pat. No. 3,934,023 discloses an insecticidal composition obtained by mixing 2-methyl-4-oxo-3-(2-propynyl)cyclopent-2-enyl (+)-chrysanthemate with 3-phenoxybenzyl (+)-chrysanthemate. EP-A1-64 803 discloses an insecticidal composition obtained by mixing three compounds, i.e., 2-methyl-4-oxo-3-(2-propenyl) (+)trans chrysanthemate, 3-phenoxybenzyl 3-(2,2-dichlorovinyl)-2,2-dimethylcyclopropanecarboxylate and N-(3,4,5,6-tetraphthalimide)methyl chrysanthemate.

Conventional insecticidal and/or acaricidal composition, however, cannot sufficiently, satisfy various requirements, and for example, they are not sufficient in lethal efficacy, immediate effect, etc.

According to the present invention, there are provided an insecticidal and/or acaricidal composition (hereinafter the present composition) comprising as active ingredients 2-methyl-4-oxo-3-(2-propynyl)-cyclopent-2-enyl chrysanthemate having the formula (hereinafter Compound [II]):

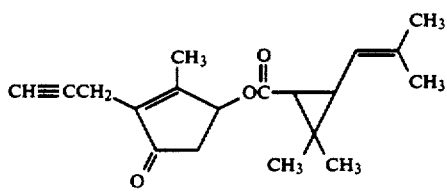

and a phenoxybenzyl ester compound having the formula [I]:

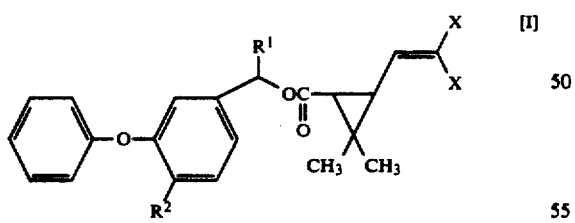

wherein R¹ is hydrogen or cyano, R² is hydrogen or fluorine, and X is chlorine or bromine; a method for controlling insects and/or acarines which comprises applying the composition; and a process for producing an oil formulation, oil-based aerosol, water-based aerosol, emulsifiable concentrate, wettable powder, aqueous emulsion concentrate, formulation for ULV application, or the like, comprising the composition.

The present composition has the following desirable properties:

(1) It has a high lethal efficacy and knockdown efficacy against insect and/or acarine pests.

(2) It shows an unexpectedly larger synergistic effect than do the compositions obtained by mixing pyrethroid compounds which have been considered to have a synergistic effect.

(3) It is markedly effective also against insect and/or acarine pests having a low sensitivity to pyrethroid.

(4) It is markedly effective also against acarine pests on which a single agent has a very low effect.

Specific examples of the phenoxybenzyl ester compound of the formula [I] are as follows:

3-phenoxybenzyl (1RS)-cis,trans-3-(2,2-dichlorovinyl)-2,2-dimethylcyclopropanecarboxylate, 3-phenoxybenzyl (1R)-trans-3-(2,2-dichlorovinyl)-2,2-dimethylcyclopropanecarboxylate, 3-phenoxybenzyl (1R)-cis-3-(2,2-dichlorovinyl)-2,2-dimethylcyclopropanecarboxylate, (RS)-α-cyano-3-phenoxybenzyl (1RS)-cis,trans-(2,2-dichlorovinyl)-2,2-dimethylcyclopropanecarboxylate, (RS)-α-cyano-3-phenoxybenzyl (1R)-trans-3-(2,2-dichlorovinyl)-2,2-dimethylcyclopropanecarboxylate, (RS)-α-cyano-3-phenoxybenzyl (1R)-cis-3-(2,2-dichlorovinyl)-2,2-dimethylcyclopropanecarboxylate, (S)-α-cyano-3-phenoxybenzyl (1RS)-cis,trans-3-(2,2-dichlorovinyl)-2,2-dimethylcyclopropanecarboxylate, (S)-α-cyano-3-phenoxybenzyl (1R)-cis-3-(2,2-dichlorovinyl)-2,2-dimethylcyclopropanecarboxylate, (RS)-α-cyano-4-fluoro-3-phenoxybenzyl 1RS)-cis,-trans-3-(2,2-dichlorovinyl)-2, 2-dimethylcyclopropanecarboxylate, (RS)-α-cyano-4-fluoro-3-phenoxybenzyl (1R)-cis-3-(2, 2-dichlorovinyl)-2,2-dimethylcyclopropanecarboxylate, (S)-α-cyano-4-fluoro-3-phenoxybenzyl (1R)-cis-3-(2, 2-dichlorovinyl)-2,2-dimethylcyclopropanecarboxylate, (S)-α-cyano-3-phenoxybenzyl (1R)-cis-3.(2,2-dibromovinyl)-2,2-dimethylcyclopropanecarboxylate.

3-Phenoxybenzyl (1RS)-trans-3-(2,2-dichlorovinyl)-2,2-dimethylcyclopropanecarboxylate, 3-Phenoxybenzyl (1RS)-cis-3-(2,2-dichlorovinyl)-2,2-dimethylcyclopropanecarboxylate, (RS)-α-cyano-3-phenoxybenzyl (1RS)-trars-3-(2,2-dichlorovinyl)-2,2-dimethylcyclopropanecarbrxylate, (RS)-α-cyano-3-phenoxybenzyl (1RS)-cis-3-(2,2-dichlorovinyl)-2,2-dimethylcyclopropanecarboxylate, (S)-α-cyano-3-phenoxybenzyl (1R)-trans-3-(2,2-dichlorovinyl)-2,2-dimethylcyclopropanecarboxylate, (S)-α-cyano-3-phenoxybenzyl (1RS)-trans-3-(2,2-dichlorovinyl)-2,2-dimethylcyclopropanecarboxylate, (S)-α-cyano-3-phenoxybenzyl (1RS)-cis-3-(2,2-dichlorovinyl)-2,2-dimethylcyclopropanecarboxylate, (S)-α-cyano-4-fluoro-3-phenoxybenzyl (1R)-trans-3-(2,2-dichlorovinyl)-2, 2-dimethylcycloproanecarboxylate.

The mixing ratio of Compound [II] to the phenoxybenzyl ester compound of the formula [I] is not critical. It is usually 95:5 to 5:95 by weight, preferably 90:10 to 10:90 by weight.

More preferably, a mixing ratio for attaining a higher lethal efficacy against insect pests is 70:30 to 10:90 by weight. A mixing ratio for attaining a higher knockdown efficacy (immediate effect) against insect pests is 90:10 to 30:70 by weight. And a mixing ratio for attaining a higher acaricidal efficacy is 90:10 to 30:70 by weight.

The present composition is effective against various insect pests and/or acarine pests. It is markedly effective particularly against hygienic pests, wood pests, clothes pests, foodstuff pests, household nuisance pests, etc.

Specific examples of insect pests and acarine pests to which the present composition can be applied are given below.

Lepidoptera

*Tinea pellionella* (casemaking clothes moth), *Tineola bisselliella* (webbing clothes moth), *Plodia interpunctella* (Indian meal moth), etc.

Diptera

Culex spp. (common mosquitoes), Anopheles spp. (Anopheline mosquitoes), Aedes spp., Muscidae (house flies), Drosophilidae (vinegar flies), Psychodidae (moth flies), etc.

Coleoptera

*Sitophilus zeamais* (maize weevil), *Callosobruchus chinensis* (adzuki bean weevil), *Tribolium castaneum* (red fluor beetle), Anobiidae (deathwatch and drugstore beetles), Lyctidae (powder post beetle:), *Psaederus fuscipes* (robe beetle), etc.

Dictyoptera

*Blattella germanica* (German cockroach), *Periplaneta fuliginosa* (smokybrown cockroach), *Periplaneta americana* (American cockroach), *Periplaneta brunnea* (brown cockroach), *Blatta orientalis* (oriental cockroach), etc.

Hymenoptera

Formicidae (ants), Bethylidae (bethylid wasps), etc.

Siphonaptera

*Pulex irritans*, etc.

Anoplura

*Pediculus humanus capitis* (body louse), *Pthirus pubis* (crab louse), etc.

Isoptera

*Reticulitermes speratus, Coptotermes formosanus* (Formosan subterranean termite), etc.

Acarina

Mites associated with house dust and stored food, such as Abcaridae, Pyroglyphidae, Cheyletidae, and the like, Ixodidae such as *Boophilus microplus*, and the like, Dermanyssidae, etc.

The present composition is applied usually after having been formulated into various formulations, for example, oil formulations, emulsifiable concentrates, wettable powders, flowable concentrates (e.g. aqueous suspension concentrates or aqueous emulsion concentrates), granules, dusts, aerosols, heating fumigants (e.g. mosquito coils, electric mosquito mats, or electric nonmat formulation, i.e. heating fumigation of such a form that a part of a porous absorptive wick is dipped in an insecticidal solution to allow it to absorb the solution and said wick is indirectly heated at the top to fumigate the absorbed insecticidal solution, heating smoking formulations (e.g. selfburning-type smoking formulations, chemical-reaction-type smoking formulations, or electrically heating-type smoking formulations), non-heating volatile formulations (e.g. resin volatile formulations, or impregnated paper volatile formulations), foggings, ULV formulations, poisonous baits, or the like, by mixing the present composition with a solid carrier, liquid carrier, gaseous carrier, or bait, or impregnating a base material such as a mosquito coil or mat with the present composition, and optionally adding auxiliaries for formulation such as surfactants and the like.

The content of the active ingredients (the sum of Compound [II] and the compound of the formula [I]) in these formulations is not critical. It is usually 0.001 to 95% by weight.

In the case of formulation into an oil formulation, the content of the active ingredients is preferably 0.001 to 1% by weight. In the case of formulation into an oil-based aerosol or a water-based aerosol, the content is preferably 0.005 to 1% by weight. In the case of formulation into an emulsifiable concentrate, a wettable powder or an aqueous emulsion concentrate, the content is preferably 2.5 to 20% by weight. In the case of formulation into a formulation for ULV application, the content is preferably 10 to 95% by weight.

The solid carrier used for formulation includes, for example, fine powders or granules of clays (e.g. kaolin clay, diatomaceous earth, synthetic hydrated silicon dioxide, bentonite, fubasami clay and acid clay), talcs, ceramics, other inorganic minerals (e.g. sericite, quartz, sulfur, activated carbon, calcium carbonate and hydrated silica), chemical fertilizers (e.g. ammonium sulfate, ammonium phosphate, ammonium nitrate, urea and ammonium chloride). The liquid carrier includes, for example, water, alcohols (e.g. methanol and ethanol), ketones (e.g. acetone, methyl ethyl ketone and cyclohexanone), aromatic hydrocarbons (e.g. benzene, toluene, xylene, ethylbenzene and methylnaphthalene), aliphatic hydrocarbons (e.g. hexane, cyclohexane, kerosene and light oil), esters (e.g. ethyl acetate and butyl acetate), nitriles (e.g. acetonitrile and isobutyronitrile), ethers (e.g. diisopropyl ether and dioxane), acid amides (e.g. N,N-dimethylformamide and N,N-dimethylacetamide), halogenated hydrocarbons (e.g. dichloromethane, trichloroethane and carbon tetrachloride), dimethyl sulfoxide, and vegetable oils (e.g. soybean oil and cotton seed oil). The gaseous carrier, i.e., propellant, includes for example, freon gas, butane gas, LPG (liquefied petroleum gas), dimethyl ether and carbon dioxide.

The surfactant includes, for example, alkyl sulfates, alkylsulfonates, alkylarylsulfonates, alkyl aryl ethers and their polyoxyethylenated products, polyethylene glycol ethers, polyhydric alcohol esters and sugar alcohol derivatives. As the surfactant, Rheodol MO-60, Rheodol SP-L10, Rheodol TW-0120W (Kao Corp.), New Kalgen 1015-H (Takemoto Oil and Fat Co., Ltd.) and Sorpol SM-200 (Toho Chemical Co., Ltd.) are commercially available.

The auxiliaries for formulation such as fixing agents and dispersants include, for example, casein, gelatin, polysaccarides (e.g. starch powder, gum arabic, cellulose derivatives and alginic acid), lignin derivatives, bentonite, saccharides, synthetic watersoluble polymers (e.g. polyvinyl alcohol, polyvinyl pyrrolidone and polyacrylic acids). As stabilizers, there can be exemplified PAP (acidic isopropyl phosphate), BHT (2,6-di-tert-butyl-4-methylphenol), BHA (a mixture of 2-tert-butyl-4-methoxyphenol and 3-tert-butyl-4-methoxyphenol), vegetable oils, mineral oils, surfactants, and fatty acids or their esters.

As base materials for the mosquito coils, there can be exemplified mixtures of vegetable powders (e.g. wood powder and Pyrethrum marc) and binders (e.g. Tabu powder, starch and gluten).

As base materials for the electric mosquito mats, there can be exemplified plates obtained by coagulating fibril of cotton linter or a mixture of cotton linter and pulp.

As base materials for the self-burning-type smoking formulations, there can be exemplified combustible and heat-generating agents (e.g. nitrates, nitrites, guanidine salts, potassium chlorate, nitrocellulose, ethylcellulose and wood powder), pyrolysis-promoting agents (e.g. alkali metal salts, alkaline earth metal salts, dichromates and chromates), oxygen-supplying agents (e.g. potassium nitrate), combustion-supporting agents (e.g. melamine and wheat starch), extending agents (e.g. diatomaceous earth) and binders (e.g. synthetic pastes).

As base materials for chemical-reaction-type smoking formulations, there can be exemplified heat-generating agents (e.g. sulfides, polysulfides, hydrosulfides and hydrate salts of alkali metals, and calcium oxide), catalysts (e.g. carbonaceous substances, iron carbide and activated clay), organic foaming agents (e.g. azodicarbonamide, benzenesulfonylhydrazide, dinitrosopentamethylenetetramine, polystyrenes and polyurethanes) and fillers (natural fiber pieces and synthetic fiber pieces).

As base materials for the volatile formulations requiring no heating, there can be exemplified thermoplastic resins, filter papers, and Japanese papers.

As base materials for the poisonous baits, there can be exemplified bait components (e.g. cereal flour, vegetable refined oils, saccharides, crystalline cellulose and dextrine) antioxidants (e.g. dibutylhydroxytoluene and nordihydroguaiaretic acid), preservatives (e.g. dehydroacetic acid), and attractants (e.g. cheese perfume, onion perfume and peanut oil). Further, red pepper powders etc. are also included as an agent for preventing children from eating the poisonous baits by mistake.

The formulation into a flowable concentrate (an aqueous suspension concentrate or an aqueous emulsion concentrate) can be carried out generally by finely dispersing Compound [II] and the compound of the formula [I] in a proportion of 1 to 75% in water containing 0.5 to 15% of a dispersant, 0.1 to 10% of a suspension assistant (e.g. a protective colloid or a compound capable of imparting thixotropy) and 0 to 10% of suitable auxiliaries (e.g. defoaming agents, rust preventors, stabilizers, spreaders, penetration assistants, antifreezing agents, bacteria-proofing agents, and mildewproofing agents). It is also possible to prepare an oil-based suspension concentrate by using an oil substantially incapable of dissolving Compound [II] and the compound of the formula [I], in place of water. As the protective colloid, there can be used, for example, gelatin, casein, gums, cellulose ether and polyvinyl alcohol. The compound capable of imparting thixotropy includes, for example, bentonite, aluminum magnesium silicate, xanthan gum and polyacrylic acids.

When the present compositions are used as an active ingredient for controlling insect and/or acarine pests, their applying dosage usually ranges from 0.01 to 10,000 mg/m$^2$ or from 0.001 to 100,000 mg/m$^3$. The formulations thus obtained are applied as they are or after dilution with water or the like. It is also possible to apply them in admixture with or independently from other insecticides, acaricides or fungicides.

The emulsifiable concentrates, wettable powders, flowable concentrates and the like are applied after dilution to 1 to 10,000 ppm with water. The oil formulations, aerosols, fumigants, smoking formulations, volatile formulations, foggings, ULV formulations, poisonous baits and the like are applied as they are.

Both the applying dosage and the applying concentration of the above formulations are varied depending on the type of formulation, when, where and how these formulations are applied, kind of pests, etc., and can be increased or decreased irrespective of the above range.

The following formulation examples and test examples serve to give specific illustration of the present invention but they are not intended in any way to limit the scope of the present invention.

In the following formulation examples and test examples, the member used for Compound [II] and the compounds of the formula [I] are indicated by the symbols shown in Table 1. In the formulation examples, parts are all by weight.

TABLE 1

| Symbol of compound | Chemical name | Common name |
| --- | --- | --- |
| [II-a] | (S)-2-Methyl-4-oxo-3-(2-propynyl)cyclopent-2-enyl (1R)-cis,trans-chrysanthemate | Prallethrin |
| [I-a] | 3-Phenoxybenzyl (1RS)-cis,trans-3-(2,2-dichlorovinyl)-2,2-dimethylcyclopropanecarboxylate | Permethrin |
| [I-b] | (RS)-α-cyano-3-phenoxybenzyl (1RS)-cis,trans-3-(2,2-dichlorovinyl)-2,2-dimethylcyclopropanecarboxylate | Cypermethrin |
| [I-s] | (RS)-α-cyano-4-fluoro-3-phenoxybenzyl (1RS)-cis,trans-3-(2,2-dichlorovinyl)-2,2-dimethylcyclopropanecarboxylate | Cyfulthrin |
| [I-d] | (S)-α-cyano-3-phenoxybenzyl (1R)-cis-3-(2,2-dibromovinyl)-2,2-dimethylcyclopropanecarboxylate | Deltamethrin |

FORMULATION EXAMPLE 1

Twenty oil formulations are obtained by mixing 1 part of a mixture of Compound [II-a] and either Compound [I-a], [I-b], [I-c] or [I-d] (mixing ratio: 90:10, 70:30, 50:50, 30:70 or 10:90 by weight) with 99 parts of kerosene to dissolve the same.

FORMULATION EXAMPLE 2 to 15

Oil formulations are obtained in the same manner as in Formulation Example 1 from x parts of a mixture of Compound [II-a] and either Compound [I-a], [I-b], [I-c] or [I-d] (mixing ratio: 90:10, 70:30, 50:50, 30:70 or 10:90 by weight) and y parts of kerosene. Values for x and y are varied as shown below. The number of oil formulations is 20 per each Formulation Example.

|  | x (active ingredient) | y (kerosene) |
| --- | --- | --- |
| Formulation Example 2 | 0.5 | 99.5 |
| Formulation Example 3 | 0.4 | 99.6 |
| Formulation Example 4 | 0.35 | 99.65 |
| Formulation | 0.3 | 99.7 |

| | x (active ingredient) | y (kerosene) |
|---|---|---|
| Formulation Example 5 | 0.25 | 99.75 |
| Formulation Example 6 | 0.2 | 99.8 |
| Formulation Example 7 | 0.15 | 99.85 |
| Formulation Example 8 | 0.1 | 99.9 |
| Formulation Example 9 | 0.075 | 99.925 |
| Formulation Example 10 | 0.05 | 99.95 |
| Formulation Example 11 | 0.025 | 99.975 |
| Formulation Example 12 | 0.01 | 99.99 |
| Formulation Example 13 | 0.005 | 99.995 |
| Formulation Example 14 | 0.001 | 99.999 |
| Formulation Example 15 | | |

FORMULATION EXAMPLE 16

Twenty oil-based aerosols are obtained by mixing 1 part of a mixture of Compound [II-a] and either Compound [I-a], [I-b], [I-c] or ]I-d] (mixing ratio: 90:10, 70:30, 50:50, 30:70 or 10:90 by weight) with 59 parts of kerosene to dissolve the same, and charging each of the resulting solution into an aerosol container, attaching a valve part to the container, and then compressing 40 parts of a propellant (liquefied petroleum gas) into the container under pressure through the valve part.

FORMULATION EXAMPLES 17 to 29

Oil-based aerosols are obtained in the same manner as in Formulation Example 16 by using x parts of a mixture of Compound [II-a] and either Compound [I-a], [I-b], [I-c] or [I-d] (mixing ratio: 90:10, 70:30, 50:50, 30:70 or 10:90 by weight), y parts of kerosene, and 40 parts of the propellant. Values for x and y are varied as shown below. The number of oil-based aerosols is 20 per each Formulation Example.

| | x (active ingredient) | y (kerosene) |
|---|---|---|
| Formulation Example 17 | 0.5 | 59.5 |
| Formulation Example 18 | 0.4 | 59.6 |
| Formulation Example 19 | 0.35 | 59.65 |
| Formulation Example 20 | 0.3 | 59.7 |
| Formulation Example 21 | 0.25 | 59.75 |
| Formulation Example 22 | 0.2 | 59.8 |
| Formulation Example 23 | 0.15 | 59.85 |
| Formulation Example 24 | 0.1 | 59.9 |
| Formulation Example 25 | 0.075 | 59.925 |
| Formulation Example 26 | 0.05 | 59.95 |
| Formulation Example 27 | 0.025 | 59.975 |
| Formulation Example 28 | 0.01 | 59.99 |
| Formulation Example 29 | 0.005 | 59.995 |

FORMULATION EXAMPLE 30

Forty water-based aerosols are obtained by mixing 1 part of a mixture of Compound [II-a] and either Compound [I-a], [I-b], [I-c] or [I-d] (mixing ratio: 90:10, 70:30, 50:50, 30:70 or 10:90 by weight), 1 part of an emulsifier [a 4:1 mixture of Rheodol MO-60 (a registered a trade name, Kao Corp.) and Theodol TW-0120 (a registered trade name, Kao Corp.), or Rheodol SP-L10 (a registered trade namer, Kao Corp.)] and 8 parts of kerosene to effect dissolution, charging each of the resulting mixtures and 50 parts of deionized water into an aerosol container, attaching a valve part to the container, and then compressing 40 parts of a propellant (liquefied petroleum gas) into the container under pressure through the valve part.

FORMULATION EXAMPLES 31 to 41

Water-based aerosols are obtained in the same manner as in Formulation Example 30 by using x parts of a mixture of Compound [II-a] and either Compound [I-a], [I-b], [I-c] or [I-d] (mixing ratio: 90:10, 70:30, 50:50, 30:70 or 10:90 by weight), 1 part of the emulsifier, y parts of kerosene, 50 parts of deionized water and 40 parts of the propellant. Values for x and y are varied as shown below. The number of aqueous aerosols is 40 per each Formulation Example.

| | x (active ingredient) | y (kerosene) |
|---|---|---|
| Formulation Example 31 | 0.5 | 8.5 |
| Formulation Example 32 | 0.4 | 8.6 |
| Formulation Example 33 | 0.3 | 8.7 |
| Formulation Example 34 | 0.2 | 8.8 |
| Formulation Example 35 | 0.15 | 8.85 |
| Formulation Example 36 | 0.1 | 8.9 |
| Formulation Example 37 | 0.075 | 8.925 |
| Formulation Example 38 | 0.05 | 8.95 |
| Formulation Example 39 | 0.025 | 8.975 |
| Formulation Example 40 | 0.01 | 8.99 |
| Formulation Example 41 | 0.005 | 8.995 |

FORMULATION EXAMPLES 42 and 43

Emulsifiable concentrates are obtained by thoroughly mixing x parts of a mixture of Compound [II-a] and either Compound [-a], [I-b], [I-c] or [I-d] (mixing ratio: 90:10, 70:30, 50:50, 30:70 or 10:90 by weight), 7 parts an emulsifier [New Kalgen 1015-H (a registered trade name, Takemoto Oil and Fat Co., Ltd.)] and y parts of xylene to effect dissolution. Values for x and y are varied as shown below. The number of emulsifiable concentrates is 20 per each Formulation Example.

|  | x (active ingredient) | y (xylene) |
|---|---|---|
| Formulation Example 42 | 2.5 | 90.5 |
| Formulation Example 43 | 5 | 88 |

FORMULATION EXAMPLES 44 and 45

Emulsifiable concentrates are obtained by thoroughly mixing x parts of a mixture of Compound [II-a] and either Compound [I-a], [I-b], [I-c] or [I-d] (mixing ratio: 90:10, 70:30, 50:50, 30:70 or 10:90 by weight), 10 parts of an emulsifier [Sorpol SM-200 (a registered trade name, Toho Chemical Co., Ltd.)] and y parts of xylene to effect dissolution. Values for x and y are varied as shown below. The number of emulsifiable concentrates is 20 per each Formulation Example.

|  | x (active ingredient) | y (xylene) |
|---|---|---|
| Formulation Example 44 | 10 | 80 |
| Formulation Example 45 | 20 | 70 |

FORMULATION EXAMPLE 46

Twenty wettable powders are obtained by adding 10 parts of a mixture of Compound [II-a] and either Compound [I-a], [I-b], [I-c] or [I-d] (mixing ratio: 90:10, 70:30, 50:50, 30:70 or 10:90 by weight) to a mixture of 4 parts of sodium lauryl sulfate, 2 parts of calcium lignosulfonate, 20 parts of synthetic hydrated silicon dioxide fine powder and 64 parts of diatomaceous earth, and stirring and mixing them in a mixer.

FORMULATION EXAMPLE 47

To 40 parts of an aqueous solution containing 6 parts of polyvinyl alcohol is added 10 parts of a mixture of Compound [II-a] and either Compound [I-a], I-b], [I-c] or [I-d] (mixing ratio: 90:10, 70:30, 0:50, 30:70 or 10:90 by weight), and stirring the resulting mixture in a mixer, whereby dispertions are obtained. To each dispersion are added 40 parts of an aqueous solution containing 0.05 part of xanthan gum and 0.1 part of aluminum magnesium silicate, and then 10 parts of propylene glycol, and gently stirring and mixing the resulting mixture, whereby 20 aqueous emulsion concentrates are obtained.

FORMULATION EXAMPLES 48 and 49

ULV formulations are obtained by thoroughly mixing x parts of a mixture of Compound [II-a] and either Compound [I-a], [I-b], [I-c] or [I-d] (mixing ratio: 90:10, 70:30, 50:50, 30:70 or 10:90 by weight) and y parts of xylene to effect dissolution. Values for x and y are varied as shown below. The number of ULV formulations is 20 per each Formulation Example.

|  | x (active ingredient) | y (xylene) |
|---|---|---|
| Formulation Example 48 | 50 | 50 |
| Formulation Example 49 | 95 | 5 |

Test examples are described below. The compositions used for comparison in the test examples were mixtures of N-(3,4,5,6-tetrahydrophthalimide)methyl (1RS)-trans-chrysanthemate (hereinafter Compound [A] and 5-(2-propynyl)furfuryl (1RS)-trans-3-(2,2-dichlorovinyl)-2,2-dimethylcyclopropanecarboxylate (hereinafter Compound [B]), which compositions are described in U.S. Pat. No. 3,899,586.

TEST EXAMPLE 1

The test described below was carried out for each of the oil formulations obtained in Formulation Examples 1 to 15, oil formulations obtained in the same manner as in said Formulation Examples except for using each compound alone, and oil formulations obtained in the same manner as in said Formulation Examples except for using the compositions for comparison.

Ten adult German cockroaches (*Blattella germanica*) (5 males and 5 females) were released in a polyethylene cup having a diameter of 9 cm whose wall surface had been thinly coated with vaseline. The polyethylene cup was closed with a 16-mesh nylon gauze and placed on the bottom of a glass cylinder having an inside diameter of 10 cm and a height of 37 cm. Each concentration of each oil formulation described above was directly sprayed in a volume of 0.6 ml with a spray gun at a pressure of 0.6 atmosphere from the upper end of the cylinder, and the knocked-down insects after the lapse of 2.5 minutes were counted. From the results obtained at various concentrations, $KC_{50}$ value (50% knockdown concentration) after 2.5 minutes was determined for each of the compositions having the respective mixing ratios. (three replications for each concentration).

Table 2 show the test results.

TABLE 2

| Active ingredient |  | $KC_{50}$ value (%) | Relative efficacy* |
|---|---|---|---|
| Compound [II-a] |  | 0.026 | 100 |
| Compound [I-a] |  | 0.53 | 4.9 |
| Compound [I-b] |  | 0.18 | 14 |
| Compound [I-c] |  | 0.16 | 16 |
| Compound [I-d] |  | 0.13 | 20 |
| Compound [A] |  | 0.11 | 23 |
| Compound [B] |  | 0.23 | 11 |
| Compound [II-a] + Compound [I-a] | 90:10 | 0.012 | 220 |
| " | 70:30 | 0.0092 | 280 |
| " | 50:50 | 0.010 | 260 |
| " | 30:70 | 0.012 | 220 |
| Compound [II-a] + Compound [I-b] | 90:10 | 0.0097 | 270 |
| " | 70:30 | 0.0081 | 320 |
| " | 50:50 | 0.0089 | 290 |
| " | 30:70 | 0.011 | 240 |
| Compound [II-a] + Compound [I-c] | 90:10 | 0.0096 | 270 |
| " | 70:30 | 0.0080 | 330 |
| " | 50:50 | 0.0088 | 300 |
| " | 30:70 | 0.010 | 260 |
| Compound [II-a] + Compound [I-d] | 90:10 | 0.0093 | 280 |
| " | 70:30 | 0.0078 | 330 |
| " | 50:50 | 0.0085 | 310 |
| " | 30:70 | 0.010 | 260 |
| Compound [A] + Compound [B] | 90:10 | 0.12 | 22 |
| " | 70:30 | 0.13 | 20 |
| " | 50:50 | 0.15 | 17 |

TABLE 2-continued

| Active ingredient | | KC$_{50}$ value (%) | Relative efficacy* |
|---|---|---|---|
| " | 30:70 | 0.18 | 14 |

*The efficacy of Compound [II-a] was taken as 100.

TEST EXAMPLE 2

The test described below was carried out for each of the water based aerosols obtained in Formulation Examples 30 to 41 (Rheodol SP-L10 was used for an emulsifier), water-based aerosols obtained in the same manner as in said Formulation Examples except for using each compound alone, and water-based aerosols obtained in the same manner as in said Formulation Examples except for using the compositions for comparison.

In accordance with the aerosol test method using a Pete Grady's chamber of 183 cm cube (6.1 m$^3$) [the method described in Soap and Chemicals Specialties Blue Book (1965)], 100 adult houseflies (*Musca domestica*) in each chamber were sprayed with 700 mg of each water-based aerosol. After the lapse of 20 minutes, the test insects were recovered. After 24 hours, the dead and alive were counted. From the mortality at each concentration, LC$_{50}$ value (50% lethal concentration) was determined for each of the compositions having the respective mixing ratios. (two replications for each concentration).

Table 3 shows the results.

TABLE 3

| Active ingredient | | KC$_{50}$ value (%) | Relative efficacy* |
|---|---|---|---|
| Compound [II-a] | | 0.11 | 100 |
| Compound [I-a] | | 0.086 | 130 |
| Compound [I-b] | | 0.031 | 350 |
| Compound [I-c] | | 0.029 | 380 |
| Compound [I-d] | | 0.014 | 790 |
| Compound [A] | | 0.40 | 28 |
| Compound [B] | | 0.18 | 61 |
| Compound [II-a] + Compound [I-a] | 70:30 | 0.039 | 280 |
| " | 50:50 | 0.038 | 290 |
| " | 30:70 | 0.033 | 330 |
| " | 10:90 | 0.036 | 310 |
| Compound [II-a] + Compound [I-b] | 70:30 | 0.014 | 790 |
| " | 50:50 | 0.014 | 790 |
| " | 30:70 | 0.012 | 920 |
| " | 10:90 | 0.013 | 850 |
| Compound [II-a] + Compound [I-c] | 70:30 | 0.013 | 850 |
| " | 50:50 | 0.013 | 850 |
| " | 30:70 | 0.011 | 1000 |
| " | 10:90 | 0.012 | 920 |
| Compound [II-a] + Compound [I-d] | 70:30 | 0.0064 | 1700 |
| " | 50:50 | 0.0061 | 1800 |
| " | 30:70 | 0.0054 | 2000 |
| " | 10:90 | 0.0060 | 1800 |
| Compound [A] + Compound [B] | 70:30 | 0.33 | 33 |
| " | 50:50 | 0.25 | 44 |
| " | 30:70 | 0.21 | 52 |
| " | 10:90 | 0.19 | 58 |

*The efficacy of Compound [II-a] was taken as 100.

TEST EXAMPLE 3

The test described below was carried out for each of the 10% emulsifiable concentrates obtained in Formulation Example 44, 10% emulsifiable concentrates obtained in the same manner as in said Formulation Example except for using each compound alone, and 10% emulsifiable concentrates obtained in the same manner as in said Formulation Example except for using the compositions for comparison.

Each of the above-mentioned emulsifiable concentrate was diluted to predetermined concentrations. A 6 cm × 12 cm filter paper was uniformly treated with 0.36 ml of each dilution, air-dried, and then folded into two, after which both ends were sticked to each other with paste to obtain a bag. In the bag were placed 20 adults of *Dermatophaqoides farinae* and diet, and the upper part of the bag was clasped with a clip to shut its mouth. Then, the bag was allowed to stand at a temperature of 25° C. and at a humidity of 65% RH After 24 hours, the dead and alive were counted. From the mortality at each dose, LD$_{50}$ value (50% lethal dose) was determined for each of the compositions having the respective mixing ratios. (two replications for each dose).

Table 4 shows the results.

TABLE 4

| Active ingredient | | KC$_{50}$ value (%) | Relative efficacy* |
|---|---|---|---|
| Compound [II-a] | | 0.18 | 100 |
| Compound [I-a] | | 0.61 | 30 |
| Compound [I-b] | | 3.2 | 5.6 |
| Compound [I-c] | | 3.0 | 6.0 |
| Compound [I-d] | | 2.0 | 9.0 |
| Compound [A] | | 5.5 | 3.3 |
| Compound [B] | | 1.1 | 16 |
| Compound [II-a] + Compound [I-a] | 90:10 | 0.051 | 350 |
| " | 70:30 | 0.040 | 450 |
| " | 50:50 | 0.045 | 400 |
| " | 30:70 | 0.057 | 320 |
| Compound [II-a] + Compound [I-b] | 90:10 | 0.077 | 230 |
| " | 70:30 | 0.060 | 300 |
| " | 50:50 | 0.068 | 260 |
| " | 30:70 | 0.087 | 210 |
| Compound [II-a] + Compound [I-c] | 90:10 | 0.076 | 240 |
| " | 70:30 | 0.059 | 310 |
| " | 50:50 | 0.067 | 270 |
| " | 30:70 | 0.086 | 210 |
| Compound [II-a] + Compound [I-d] | 90:10 | 0.068 | 260 |
| " | 70:30 | 0.041 | 440 |
| " | 50:50 | 0.060 | 300 |
| " | 30:70 | 0.077 | 230 |
| Compound [A] + Compound [B] | 90:10 | 4.9 | 3.6 |
| " | 70:30 | 3.4 | 5.3 |
| " | 50:50 | 2.0 | 9.0 |
| " | 30:70 | 1.3 | 14 |

*The efficacy of Compound [II-a] was taken as 100.

TEST EXAMPLE 4

The test described below was carried out for each of the oil-based aerosols obtained in Formulation Examples 16 to 29, oilbased aerosols obtained in the same manner as in said Formulation Examples except for using each compound alone, and oil-based aerosols obtained in the same manner as in said Formulation Examples except for using the compositions for comparison.

In accordance with the aerosol test method using a Pete Grady's chamber of 183 cm cube (6.1 m$^3$), 100 adult houseflies (*Musca domestica*) having a low sensitivity to pyrethroid in each chamber were sprayed with 700 mg of each oil-based aerosol. After the lapse of 5 minutes, the knocked-down insects were counted. From the results obtained at various concentrations, KC$_{50}$ value (50% knock-down concentration) after 5 minutes was determined for each of the compositions having the respective mixing ratios. (two replications for each concentration).

Table 5 shows the test results.

TABLE 5

| Active ingredient | | $KC_{50}$ value (%) | Relative efficacy* |
|---|---|---|---|
| Compound [II-a] | | 0.47 | 100 |
| Compound [I-a] | | >1 | <47 |
| Compound [I-b] | | >1 | <47 |
| Compound [I-c] | | >1 | <47 |
| Compound [I-d] | | >1 | <47 |
| Compound [A] | | >1 | <47 |
| Compound [B] | | >1 | <47 |
| Compound [II-a] + Compound [I-a] | 90:10 | 0.17 | 280 |
| " | 70:30 | 0.14 | 340 |
| " | 50:50 | 0.15 | 310 |
| " | 30:70 | 0.19 | 250 |
| Compound [II-a] + Compound [I-b] | 90:10 | 0.13 | 360 |
| " | 70:30 | 0.10 | 470 |
| " | 50:50 | 0.12 | 390 |
| " | 30:70 | 0.14 | 340 |
| Compound [II-a] + Compound [I-c] | 90:10 | 0.13 | 360 |
| " | 70:30 | 0.10 | 470 |
| " | 50:50 | 0.11 | 430 |
| " | 30:70 | 0.14 | 340 |
| Compound [II-a] + Compound [I-d] | 90:10 | 0.12 | 390 |
| " | 70:30 | 0.096 | 490 |
| " | 50:50 | 0.11 | 430 |
| " | 30:70 | 0.13 | 360 |
| Compound [A] + Compound [B] | 90:10 | >1 | <47 |
| " | 70:30 | >1 | <47 |
| " | 50:50 | >1 | <47 |
| " | 30:70 | >1 | <47 |

*The efficacy of Compound [II-a] was taken as 100.

What is claimed is:

1. An insecticidal and/or acaricidal consisting of essentially of, as active ingredient, 2-methyl-4-oxo-3(2-propynl) cyclopent-2- enyl chrysanthemate and phenoxybenzyl ester selected from the group consisting of 3-phenoxybenzyl-3-(2,2-dichlorovinyl)-2,2-dimethylcyclopropane carboxylate, α-cyano-3-phenoxybenzyl-3(2,2-dichlorovinyl)-2,2-dimethylcyclopropane carboxylate, α-cyano-fluoro-3-phenoxybenzyl-3-(2,2-dichlorovinyl)-2,2,-dimethylcyclopropane carboxylate and α-cyano-3-phenoxybenzyl-3-(2,2-dibromovinyl)-2,2-dimethylcyclopropane carboxylate; and an inert carrier; wherein the mixing ratio of 2-methyl-4-oxo-3-(2-propynyl) cyclopent-2-enyl chrysanthemate to the phenoxybenzyl ester compound is from 90:10 to 30:70.

2. The composition of claim 1, wherein the mixing ratio of 2-methyl-4-oxo-3-(2-propynyl)cyclopent-2-enyl chrysanthemate to the phenoxybenzyl ester compound having the formula [I] is 90:10 to 30:70 by weight, and the composition has a high knock-down activity against insect pests.

3. The composition of claim 1, wherein the mixing ratio of 2-methyl-4-oxo-3(2-propynyl)cyclopent-2-enyl chrysanthemate to the phenoxybenzyl ester compound having the formula [I] is 90:10 to 30:70 by weight, and the composition has a high acaricidal activity.

4. The composition of claim 1, wherein the phenoxybenzyl ester compound is 3-phenoxybenzyl 3-(2,2-dichlorovinyl)-2,2-dimethylcyclopropanecarboxylate.

5. The composition of claim 1, wherein the phenoxybenzyl ester compound is α-cyano-3-phenoxybenzyl 3-(2,2-dichlorovinyl)-2,2-dimethylcyclopropanecarboxylate.

6. The composition of claim 1, wherein the phenoxybenzyl ester compound is α-cyano-4-fluoro-3-phenoxybenzyl 3-(2,2-dichlorovinyl)-2,2-dimethylcyclopropanecarboxylate.

7. The composition of claim 1, wherein the phenoxybenzyl ester compound is α-cyano-3-phenoxybenzyl 3-(2,2-dibromovinyl)-2,2-dimethylcyclopropanecarboxylate.

8. A method for controlling insects and/or acarines comprising applying an insecticidally and/or acaricidally effective amount of an insecticidal and/or acaricidal composition according to claim 1 to insects and/or acarines.

* * * * *

UNITED STATES PATENT AND TRADEMARK OFFICE
CERTIFICATE OF CORRECTION

PATENT NO. : 5,091,183
DATED : FEBRUARY 25, 1992
INVENTOR(S) : Toshihiko Yano, et al It is certified that error appears in the above-indentified patent and that said Letters Patent is hereby corrected as shown below:

IN THE CLAIMS

Column 13, line 31, insert --composition-- after "acaricidal"; and delete "of";

line 33, insert --a-- after "and line 36, change "clopropane carboxylate" to --clopropanecarboxylate--;

line 37, change "dimethylcyclopropane carbox" to --dimethylcyclopropanecarboxylate--;

line 38, delete "ylate";

insert -- 4- -- after "-cyano-" and before "fluoro";

UNITED STATES PATENT AND TRADEMARK OFFICE
CERTIFICATE OF CORRECTION

PATENT NO. : 5,091,183
DATED : February 25, 1992
INVENTOR(S) : Toshihiko Yano, et al It is certified that error appears in the above-indentified patent and that said Letters Patent is hereby corrected as shown below:

Column 14, line 1, change "dimethylcyclopropane carboxylate" to --dimethylcyclopropanecarboxylate--.

line 3, change "dimethylcyclopropane carboxylate" to --dimethylcyclopropanecarboxylate--.

Signed and Sealed this

Nineteenth Day of September, 1995

Attest:

BRUCE LEHMAN

*Attesting Officer*       *Commissioner of Patents and Trademarks*